United States Patent [19]

Morozowich

[11] 4,001,306

[45] Jan. 4, 1977

[54] PROSTAGLANDIN F$_{2\alpha}$ 15-MONOACRYLATES

[75] Inventor: Walter Morozowich, Kalamazoo, Mich.

[73] Assignee: The Upjohn Company, Kalamazoo, Mich.

[22] Filed: Jan. 30, 1975

[21] Appl. No.: 545,366

Related U.S. Application Data

[63] Continuation-in-part of Ser. No. 214,472, Dec. 30, 1971, abandoned.

[52] U.S. Cl. .................. 260/488 R; 260/247.2 B; 260/268 R; 260/286 R; 260/293.65; 260/326.8; 260/408; 260/410; 260/429.9; 260/439 R; 260/448 R; 260/462 C; 260/468 D; 260/469; 260/471 R; 260/472; 260/473 G; 260/476 R; 260/487; 260/491; 424/287; 424/180; 424/248; 424/250; 424/289; 424/267; 424/274; 424/295; 424/305; 424/308; 424/309; 424/310; 424/311; 424/312

[51] Int. Cl.$^2$ ...................................... C07C 177/00

[58] Field of Search .......... 260/472, 448 R, 488 R, 260/429.9, 410, 514 D, 247.2 B, 293.65, 268 R, 211 R, 439 R, 326.8

[56] References Cited

UNITED STATES PATENTS

| | | | |
|---|---|---|---|
| 3,706,789 | 12/1972 | Bergstrom et al. | 260/488 R |
| 3,772,350 | 11/1973 | Pike et al. | 260/448.8 R |
| 3,821,291 | 6/1974 | Lincoln, Jr. et al. | 260/514 D |

FOREIGN PATENTS OR APPLICATIONS

| | | | |
|---|---|---|---|
| 2,262,608 | 7/1973 | Germany | 260/468 D |

*Primary Examiner*—Vivian Garner
*Attorney, Agent, or Firm*—Morris L. Nielsen

[57] ABSTRACT

Mono(carboxyacylates) of prostaglandins $F_{1\alpha}$, $F_{2\alpha}$, $F_{3\alpha}$, dihydro $F_{1\alpha}$, and their 15$\beta$ isomers, at the C-15 position, and processes for preparing them. These compounds are useful for a variety of pharmacological purposes, including inhibition of platelet aggregation, increase of nasal patency, labor inducement at term, and controlling blood pressure.

3 Claims, No Drawings

PROSTAGLANDIN Fα 15-MONOACRYLATES

CROSS REFERENCE TO RELATED APPLICATIONS

This application is a continuation-in-part of my copending application Ser. No. 214,472, filed Dec. 30, 1971, now abandoned.

BACKGROUND OF THE INVENTION

This invention relates to compositions of matter and to methods for producing them. The several aspects of this invention relate to novel derivatives of some of the known prostaglandins, for example, prostaglandin $F_{1\alpha}$ ($PGF_{1\alpha}$), prostaglandin $F_{2\alpha}$ ($PGF_{2\alpha}$), prostaglandin $F_{3\alpha}$ ($PGF_{3\alpha}$), prostaglandin dihydro $F_{1\alpha}$ (dihydro-$PGF_{1\alpha}$), their 15β epimers, and their racemates, and to novel methods for producing those novel prostaglandin-type derivatives. In particular the novel prostaglandin-type derivatives of this invention are carboxyacylated at the C-15 position.

Each of the above-mentioned known prostaglandins is a derivative of prostanoic acid which has the following structure and atom numbering:

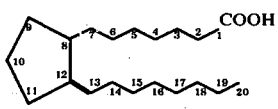

I

A systematic name for prostanoic acid is 7-[(2β-octyl)-cyclopent-1α-yl]heptanoic acid.

$PGF_{1\alpha}$ has the following structure:

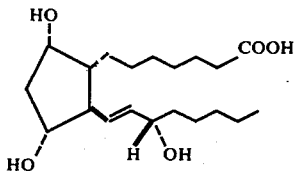

II $PGF_{2\alpha}$ has the following structure:

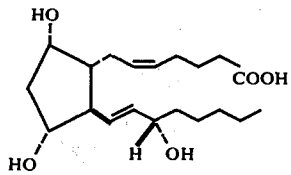

III $PGF_{3\alpha}$ has the following structure:

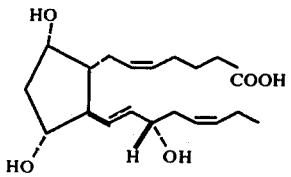

IV

Dihydro-$PGF_{1\alpha}$ has the following structure:

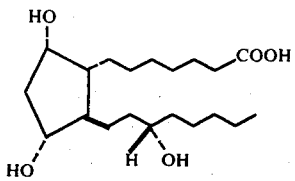

V

The prostaglandin formulas mentioned above each have several centers of asymmetry. Each formula represents the particular optically active form of the prostaglandin obtained from certain mammalian tissues, for example, sheep vesicular glands, swine lung, and human seminal plasma, or by reduction or dehydration of a prostaglandin so obtained. See, for example, Bergstrom et al., Pharmacol. Rev. 20, 1 (1968), and references cited therein. The mirror image of each formula represents a molecule of the enantiomer of that prostaglandin. The racemic form of the prostaglandin consists of equal numbers of two types of molecules, one represented by one of the above formulas and the other represented by the mirror image of that formula. Thus, both formulas are needed to define a racemic prostaglandin. See Nature 212, 38 (1966) for discussion of the stereochemistry of the prostaglandins. For convenience hereinafter, use of the terms "$PGF_{1\alpha}$", "$PGF_{2\alpha}$", and the like, will mean the optically active form of that prostaglandin with the same absolute configuration as $PGE_1$ obtained from mammalian tissues. When reference to the racemic form of any of these prostaglandins is intended, either the word "racemic" or the prefix "dl" will precede the prostaglandin name, thus, "racemic $PGF_{1\alpha}$" or "dl-$PGF_{2\alpha}$" and the like.

In formulas I, II, III, IV, and V, as well as in the formulas given hereinafter, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring.

Furthermore, in formulas II-V, the broken line attachment of the hydroxy to the C-15 carbon atom indicates the alpha configuration, i.e. below the plane of the paper. Hereinafter, compounds with epi (R) configuration for the hydroxy at C-15 are so designated by using "15-beta" in the name. If 15-beta (15β) does not appear in the name, the natural configuration for the C-15 hydroxy, identified as the S configuration for $PGE_1$, to be assumed.

$PGF_{1\alpha}$, $PGF_{2\alpha}$, $PGF_{3\alpha}$, and dihydro-$PGF_{1\alpha}$ and their esters and pharmacologically acceptable salts, are extremely potent in causing various biological responses. For that reason, these compounds are useful for pharmacological purposes. See, for example, Bergstrom et al., Pharmacol. Rev. 20, 1 (1968), and references cited therein. A few of those biological responses are systemic arterial blood pressure raising in the case of the $PGF_\alpha$ compounds as measured, for example, in anesthetized (pentobarbital sodium) pentolinium-treated rats with indwelling aortic and right heart cannulas; stimulation of smooth muscle as shown, for example, by tests on strips of guinea pig ileum, rabbit duodenum, or gerbil colon; potentiation of other smooth muscle stimulants; activity on the central nervous system; decrease of blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds are useful in mammals, including man, as nasal decongestants. For this purpose, the compounds are used in a dose range of about 10 μg. to about 10 mg. per ml. of a pharmacologically suitable liquid vehicle or as an aerosol spray, both for topical application.

The PGFα compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

The PGFα compounds are especially useful as additives to blood, blood products, blood substitutes, and other fluids which are used in artificial extracorporeal circulation and perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about .001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

The PGFα compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 μg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

The PGFα compounds are useful for controlling the reproductive cycle in ovulating female mammals, including humans and animals such as monkeys, rats, rabbits, dogs, cattle, and the like. By the term ovulating female mammals is meant animals which are mature enough to ovulate but not so old that regular ovulation has ceased. For that purpose, $PGF_{2\alpha}$, for example, is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine are alternative routes of administration. Additionally, expulsion of an embryo or a fetus is accomplished by similar administration of the compound during the first third of the normal mammalian gestation period.

SUMMARY OF THE INVENTION

It is a purpose of this invention to provide novel 15-carboxyacylated prostaglandin-type compounds. It is a further purpose to provide a novel process for preparing such compounds.

The novel prostaglandin derivatives of this invention each have a carboxyacyl group replacing the hydrogen of the C-15 hydroxyl of a PGFα -type compound. By "carboxyacyl" I mean an acyl group derived from formic acid or from a hydrocarbon carboxylic acid or a substituted hydrocarbon carboxylic acid. Hereinafter the carboxyacyl group is represented by

wherein $R_2$ is hydrogen; alkyl of one to 17 carbon atoms, inclusive; alkyl of one to 12 carbon atoms, inclusive, substituted with one to 3 halo atoms, inclusive, phenyl, phenoxy, or cycloalkyl of 3 to 7 carbon atoms, inclusive; phenyl; phenyl substituted with one to 5 halo atoms, inclusive, trifluoromethyl, nitro, phenyl, or alkyl of one to 8 carbon atoms, inclusive; or naphthyl.

This invention relates not only to the acid form of each of these prostaglandin-type derivatives but to its alkyl esters and to its pharmacologically acceptable salts, as will be hereinafter defined. Furthermore, this invention relates not only to the optically active isomer depicted by each of the formulas as drawn, but to the racemate consisting of that optically active isomer and its mirror image.

There is therefore provided by this invention an optically active compound of the formula

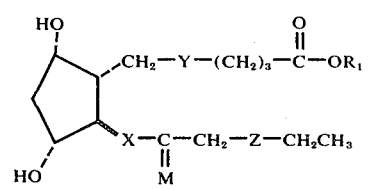

or a racemic compound of that formula and the mirror image thereof, wherein (a) X is trans—CH=CH— or —CH₂CH₂—, and Y and Z are both —CH₂CH₂—, or (b) X is trans—CH=CH—, Y is cis—CH=CH—, and Z is —CH₂CH₂— or cis—CH=CH—; wherein M is

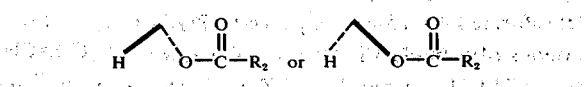

wherein R₂ is as defined above, and wherein R₁ is hydrogen or alkyl of one to 8 carbon atoms, inclusive, with the proviso that R₁ is not methyl when R₂ is methyl, X is trans—CH=CH—, Y is cis—CH=CH—, and Z is —CH₂CH₂—; and the pharmacologically acceptable salts thereof when R₁ is hydrogen.

The above generalized formula is used for convenience to represent the 15-carboxyacylates of the eight main types of prostaglandin-type compounds of this invention. By appropriate selection of M, X, Y, or Z in formula VI, there are represented the 15-carboxyacylates of PGF₁α, PGF₂α, PGF₃α, dihydro-PGF₁α, and their 15β epimers within the scope of this invention. Thus, for example, when M is

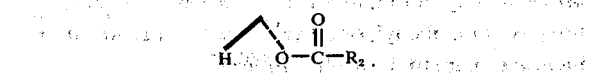

X is trans—CH=CH—, Y is cis—CH=CH—, and Z is —CH₂CH₂—, there is represented a 15-carboxyacylate of a PGF₂α-type compound:

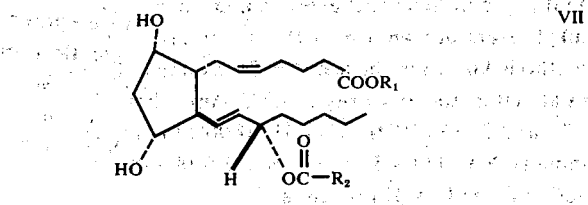

With regard to formula VI, examples of alkyl of one to 8 carbon atoms, inclusive, are methyl, ethyl, propyl, butyl, pentyl, hexyl, heptyl, octyl, and isomeric forms thereof. Examples of alkyl of one to 12 carbon atoms, inclusive, are those given above, and nonyl, decyl, undecyl, dodecyl, and isomeric forms thereof. Examples of alkyl of one to 17 carbon atoms, inclusive, are those given above, and tridecyl, tetradecyl, pentadecyl, hexadecyl, heptadecyl, and isomeric forms thereof. Examples of alkyl of one to 12 carbon atoms, inclusive, substituted with one to 3 halo atoms, inclusive, phenyl, phenoxy, or cycloalkyl of 3 to 7 carbon atoms, inclusive, include chloromethyl, dichloromethyl, trichloromethyl, bromchloromethyl, trifluoromethyl, 2-bromoethyl, 2-iodoethyl, 2-bromo-1,1-dimethylethyl, 2-chlorobutyl, 4,4,4-trichlorobutyl, nonafluorobutyl, 8-bromooctyl, 2-(2-bromoethyl)-3,7-dimethyloctyl, 12-chlorododecyl, cyclopropylmethyl, cyclohexylmethyl, 2-(cyclopentyl)ethyl, 2-(cycloheptyl)ethyl, 4-(cyclopropyl)butyl, 8-(cyclohexyl)hexyl, 12-(cyclopentyl)-dedecyl, phenylmethyl, diphenylmethyl, triphenylmethyl, 1-phenylethyl, 2-phenylethyl, 1,2-diphenylethyl, 2-phenylbutyl, 4-phenylbutyl, 1,3-dimethyl-3-phenylbutyl, 8-phenyloctyl, 12-phenyldodecyl, phenoxymethyl, and 4-phenoxybutyl.

Examples of phenyl substituted with one to 5 halo atoms, inclusive, trifluoromethyl, nitro, phenyl or alkyl of one to 8 carbon atoms, inclusive, include (o, m, or p)-bromophenyl, (o, m, or p)-chlorophenyl, (o, m, or p)-iodophenyl, 2,4 (or 3,4)-dichlorophenyl, 3,5-dibromophenyl, tetrachlorophenyl, p-trifluoromethylphenyl, 2-chloro-3-nitrophenyl, 2-chloro-4-nitrophenyl, (o, m, or p)-nitrophenyl, 2,4 (or 3,5)-dinitrophenyl, (o, m, or p)-tolyl, 2,3 (or 2,5)-dimethylphenyl, 4-methyl-3-nitrophenyl, 3,4-dimethyl-2(or 5)-nitrophenyl, 4-octylphenyl, (2,3, or 4)-biphenyl, 3-chloro-4-biphenyl, and 5-isopropyl-6-nitro-3-biphenyl.

The novel formula-VI 15-carboxyacylates of this invention each cause the biological responses described above for the PGFα compounds, and each of these novel compounds is accordingly useful for the above-described corresponding purposes, and is used for those purposes in the same manner as described above.

The known PGFα compounds uniformly cause multiple biological responses even at low doses. For example, PGF₁α and PGF₂α both cause smooth muscle stimulation at the same time they exert hypertensive activity. Moreover, for many applications, these known prostaglandins have an inconveniently short duration of biological activity. In striking contrast, the novel prostaglandin derivatives of formula VI are substantially more specific with regard to potency in causing prostaglandin-like biological responses, and have a substantially longer duration of biological activity. Therefore, each of these novel prostaglandin derivatives is surprisingly and unexpectedly more useful than one of the corresponding above-mentioned known prostaglandins for at least one of the pharmacological purposes indicated above for the latter, because it has a different and narrower spectrum of biological activity than the known prostaglandin, and therefore is more specific in its activity and causes smaller and fewer undesired side effects than the known prostaglandin. Moreover, because of its prolonged activity, fewer and smaller doses of the novel prostaglandin derivative can frequently be used to attain the desired result.

Preferred for the above purposes are the prostaglandin derivatives of this invention wherein R₂ is hydrogen; alkyl of one to 17 carbon atoms, inclusive; alkyl of one to 12 carbon atoms, inclusive, substituted with one to 3 halo atoms, inclusive, or phenoxy; or phenyl substituted with one to 5 halo atoms, inclusive, or nitro. Especially preferred are the prostaglandin derivatives of this invention wherein R₂ is alkyl of one to 17 carbon atoms, inclusive, or phenyl substituted with nitro.

Another advantage of the novel compounds of this invention, especially the preferred compounds defined hereinabove, compared with the known prostaglandins, is that these novel compounds are administered effectively orally, sublingually, intravaginally, buccally, or rectally, in addition to usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible selfadministration by the patient.

The PGFα type compounds encompassed by formula VI including the special classes of compounds described above, are used for the purposes described above in the free acid form, in ester form, or in pharmacologically acceptable salt form. When the ester form is used, the ester is any of those within the above definition of $R_1$. However, it is preferred that the ester be alkyl of one to four carbon atoms, inclusive. Of those alkyl, methyl and ethyl are especially preferred for optimum absorption of the compound by the body or experimental animal system.

Pharmacologically acceptable salts of these formula VI compounds wherein $R_1$ is hydrogen are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

As discussed above, the compounds of formula VI are administered in various ways for various purposes; e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For that purpose, it is preferred because of increased water solubility that $R_1$ in the formula-VI compound be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral or sublingual administration. For rectal or vaginal administration, suppositories prepared as known in the art are used. For tissue implants, a sterile tablet or silicone rubber capsule or other object containing or impregnated with the substance is used.

The PGF$_\alpha$ -type derivatives encompassed by formula VI are produced by the reactions and procedures described and exemplified hereinafter.

Reference to Chart A herein will make clear the steps by which PGF$_\alpha$ type compounds of formula VIII are transformed to 15-carboxyacylate PGF$_\alpha$ -type compounds of formula VI. Therein, X is trans—CH=CH— or —CH$_2$CH$_2$— when Y and Z are both —CH$_2$CH$_2$—, or X is trans—CH=CH— when Y is cis—CH=CH— and Z is —CH$_2$CH$_2$— or cis —CH=CH—;

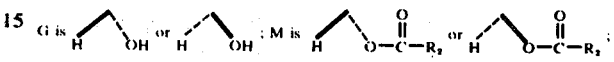

$R_1$ and $R_2$ are as defined above; and $R_3$ is alkyl of one to 12 carbon atoms, inclusive; alkyl of one to 12 carbon atoms, inclusive, substituted with one to 3 halo atoms, inclusive, amino, phenyl, trimethylsilyl, or alkoxy of one to 4 carbon atoms, inclusive; phenyl; phenyl substituted with one to 5 halo atoms, inclusive, nitro, hydroxy, alkoxy of one to 4 carbon atoms, inclusive, carboxy, amino, phenyl, or alkyl of one to 8 carbon atoms, inclusive; naphthyl; or phenanthryl.

Examples of alkyl, substituted alkyl, and substituted phenyl are given above.

The initial optically active reactants of formula VIII in Chart A, i.e., PGF$_{1\alpha}$, PGF$_{2\alpha}$, PGF$_{3\alpha}$, dihydro-PGF$_{1\alpha}$ and their 15β-epimers and the corresponding alkyl esters are known in the art or are prepared by methods known in the art. See, for example, Bergstrom et al., cited above, Corey et al., J. Am. Chem. Soc. 92, 397 and 2586 (1970), and 93, 1490 (1971), and U.S. patents No. 3,069,322 and No. 3,598,858. Optically active formula-VIII reactants

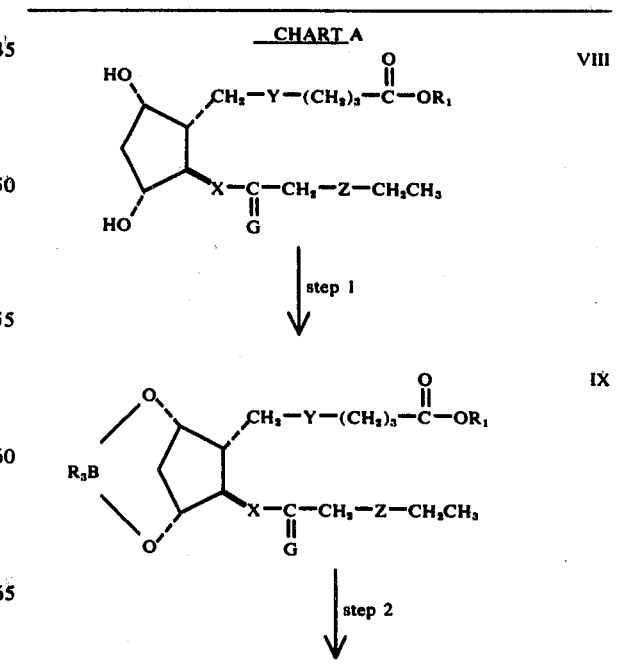

-continued

CHART A

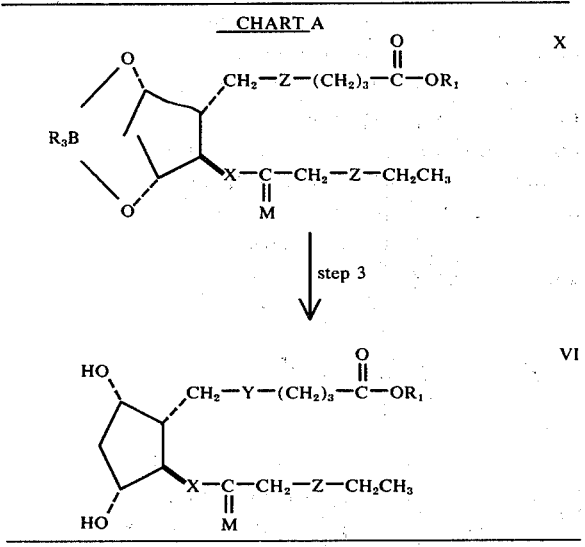

yield optically active formula-VI products.

Likewise, the initial racemic reactants of formula VIII in Chart A, i.e., racemic PGF$_{1\alpha}$, racemic PGF$_{2\alpha}$, racemic PGF$_{3\alpha}$ and their 15$\beta$-epimers and the corresponding alkyl esters are known in the art or are prepared by methods known in the art. See, for example, Just et al., J. Am. Chem. Soc. 91, 5364 (1969), Corey et al., J. Am. Chem. Soc. 90, 3245 (1968) and 91, 5675 (1969), Schneider et al., Chemical Communications (Great Britain), 304 (1969), and Axen, Chemical Communications, 602 (1970). Racemic dihydro-PGF$_{1\alpha}$ and its esters are prepared by catalytic hydrogenation of the corresponding racemic PGF$_{1\alpha}$ or PGF$_{2\alpha}$ compounds, for example, in the presence of 5% palladiumon-charcoal catalyst in ethyl acetate solution at 25° C. and one atmosphere pressure of hydrogen.

Racemic formula-VIII reactants yield racemic formula-VI products. These are useful per se, or when an optically active product is desired, they may be resolved by methods known in the art, for example, by reacting the free acids with an optically active base, e.g. brucine or strychnine, separating the resulting diastereoisomers, and recovering the corresponding optically active free acids.

Each of the 15$\beta$-epimers of 15(R) configuration is conveniently obtained by isomerizing a compound of 15(S) configuration and thereafter separating the 15(R) compound from the 15(S) compound in the mixture, for example by chromatography, as known in the art. See Pike et al., J. Org. Chem. 34, 3552 (1969). For example, oxidation of PGF$_{1\alpha}$ or PGE$_1$ with manganese dioxide gives the corresponding 15-oxo compounds. Reduction of 15-oxo-PGF$_{1\alpha}$ with sodium borohydride gives a mixture of PGF$_{1\alpha}$ and 15$\beta$-PGF$_{1\alpha}$, separable by silica gel chromatography. Likewise PGE$_1$ yields a mixture of PGE$_1$ and 15$\beta$-PGE$_1$, which are separable. Alternately, PGF$_{1\alpha}$ or PGE$_1$ are isomerized with formic acidsodium formate at 25° C. for several hours, followed by base treatment, and subsequent chromatographic separation of the respective PG and 15$\beta$-PG compounds.

Considering step 1 of Chart A, a formula-VIII PGF$\alpha$ compound is transformed to a cyclic boronate of formula IX by reaction with a boronic acid. Surprisingly, I have found that esterification occurs substantially only in the C-9 and C-11 positions. For this purpose, boronic acids of the formula R$_3$B(OH)$_2$ are used, wherein R$_3$ is as defined above.

Examples of alkyl of one to 12 carbon atoms, inclusive, substituted with one to 3 halo atoms, inclusive, amino, phenyl, trimethylsilyl, or alkoxy of one to 4 carbon atoms, inclusive, are, in addition to those given herein above, trimethylsilylmethyl, 2-trimethylsilylethyl, methoxymethyl, propoxymethyl, 1,1-dimethoxyethyl, 1,2-diethoxyethyl, 1-chloro-2,2-diethoxyethyl, 2-butoxyethyl, 8,8-dibutoxyoctyl, aminomethyl, 2-aminoethyl, 3-aminobutyl, 4-aminobutyl, 4-aminododecyl, and 12-aminododecyl.

Examples of phenyl substituted with one to 5 halo atoms, inclusive, nitro, hydroxy, alkoxy of one to 4 carbon atoms, inclusive, carboxy, amino, phenyl or alkyl of one to 8 carbon atoms, inclusive, include, in addition to those given herein above, (o, m, or p)-hydroxyphenyl, (2,4, or 6)-hydroxy-(2,3, or 4)-biphenyl, 3-hydroxy-2-nitrophenyl, 2-hydroxy-5-bromophenyl, 2-methoxy-5-bromophenyl, 4-butoxy-3-chloro-5-methoxyphenyl, 4-butoxy-3,5-diiodophenyl, 4-butoxy-2,6-dimethylphenyl, 3-butoxy-4-nitrophenyl, (o, m, or p)-carboxyphenyl, (o, m, or p)-aminophenyl, 3-amino-4-bromophenyl, 4-amino-2-ethoxyphenyl, and 3-amino-2-biphenyl.

Such boronic acids are known in the art or readily obtainable by methods known in the art. See W. Gerrard, "The Organic Chemistry of Boron", Academic Press, New York, 1961. Examples of useful boronic acids are: n-butaneboronic acid, methaneboronic acid, hexaneboronic acid, decaneboronic acid, benzeneboronic acid, p-bromobenzeneboronic acid, o-tolueneboronic acid, p-nitrobenzeneboronic acid, and 4-biphenylboronic acid. Preferred are boronic acids wherein R$_3$ is alkyl of one to 12 carbon atoms, inclusive; alkyl of one to 12 carbon atoms, inclusive, substituted with phenyl or alkoxy of one to 4 carbon atoms, inclusive; phenyl; phenyl substituted with phenyl; naphthyl; or phenanthryl. Especially preferred are boronic acids wherein R$_3$ is alkyl of one to 12 carbon atoms, inclusive.

The cyclic boronate is prepared using a mole ratio of boronic acid to PGF $\alpha$ compound in the range of one to 10, preferably about 2. Generally, moisture is excluded and the reactants are preferably in an anhydrous state. The reactants are preferably diluted with an inert, non-hydroxylic solvent, for example pyridine, acetonitrile, acetone, or N,N-dimethylformamide. Pyridine is the preferred solvent when the cyclic boronate is not isolated, because the subsequent acylation step may also be conducted in pyridine. The reaction proceeds smoothly at about 25° C. but may be carried out at either higher or lower temperatures. At high temperatures some side reactions may occur, whereas at low temperatures the rate of reaction is undesirably slow. The reaction is monitored by gas chromatography after conversion of the sample to the trimethylsilyl derivative. Depending upon the solvent and reaction temperature, the time for completing the reaction is in the range of 0.1–24 hours. The product may be isolated, for example, by removing the solvent under reduced pressure or it may be used directly in solution for the next step.

Consider, next, step 2 of Chart A, wherein the formula-IX 9,11-boronate intermediate is carboxyacylated to compound X, wherein the acyl group at C-15 is

Carboxyacylating agents useful for this transformation are known in the art or readily obtainable by methods known in the art, and include carboxyacyl halides, preferably chlorides, bromides, or fluorides, i.e. $R_2C(O)Cl$, $R_2C(O)Br$, or $R_2C(O)F$, and carboxyacid anhydrides,

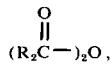

wherein $R_2$ is as defined above. The preferred reagent is an acid anhydride. Examples of acid anhydrides useful for this purpose are acetic anhydride, propionic anhydride, butyric anhydride, pentanoic anhydride, nonanoic anhydride, tridecanoic anhydride, stearic anhydride, (mono, di, or tri) chloroacetic anhydride, 3-chlorovaleric anhydride, 3-(2-bromoethyl)-4,8-dimethylnonanoic anhydride, cyclopropaneacetic anhydride, 3-cycloheptanepropionic anhydride, 13-cyclopentanetridecanoic anhydride, phenylacetic anhydride, (2 or 3)-phenylpropionic anhydride, 13-phenyltridecanoic anhydride, phenoxyacetic anhydride, benzoic anhydride, (o, m, or p)-bromobenzoic anhydride, 2,4 (or 3,4)-dichlorobenzoic anhydride, p-trifluoromethylbenzoic anhydride, 2-chloro-3-nitrobenzoic anhydride, (o, m, or p)-nitrobenzoic anhydride, (o, m, or p)-toluic anhydride, 4-methyl-3-nitrobenzoic anhydride, 4-octylbenzoic anhydride, (2,3, or 4)-biphenylcarboxylic anhydride, 3-chloro-4-biphenylcarboxylic anhydride, 5-isopropyl-6-nitro-3-biphenylcarboxylic anhydride, and (1 or 2)-naphthoic anhydride. The choice of anhydride depends upon the identity of $R_2$ in the final acylated product, for example when $R_2$ is to be methyl, acetic anhydride is used; when $R_2$ is to be 2-chlorobutyl, 3-chlorovaleric anhydride is used.

The carboxyacylation is advantageously carried out by mixing the hydroxy compound and the acid anhydride, preferably in the presence of a tertiary amine such as pyridine or triethylamine. A substantial excess of the anhydride is used, preferably about 10 to 1,000 moles of anhydride per mole of the hydroxy compound reactant. The excess anhydride serves as a reaction diluent and solvent. An inert organic diluent, for example, N,N-dimethylformamide, chloroform, ether, acetonitrile, ethyl acetate, or nitromethane, can also be added. It is preferred to use enough of the tertiary amine to neutralize the carboxylic acid produced by the reaction, as well as any free carboxyl groups present in the hydroxy compound reactant.

The reaction is preferably carried out in the range about 0° to about 100° C. The necessary reaction time will depend on such factors as the reaction temperature, and the nature of the anhydride and tertiary amine reactants. With acetic anhydride, pyridine, and a 25° C. reaction temperature, a 12 to 24-hour reaction time is used.

When $R_2$ is hydrogen,

Formylation is carried out by procedures known in the art, for example, by reaction of the hydroxy compound with the mixed anhydride of acetic and formic acids or with formylimidazole. See, for example, Fieser et al., Reagents for Organic Synthesis, John Wiley and Sons, Inc., pp. 4 and 407 (1967) and references cited therein.

In step 3 of Chart A the boronic acid moiety of the formula-X acylated boronate of step b is removed by hydrolysis to yield the formula-VI 15-carboxyacylated PGF-type derivative. Removal of the boronic acid is done with water or hydroxylic solvents such as alcohols or glycols. The preferred reagent is a methanol-water mixture (1:1 by volume). At about 25° C. a time period of one hour is sufficient to remove n-butaneboronic acid in methanol-water. The formula-VI product is isolated by conventional means, such as solvent partition with water using immiscible solvents, for example ethyl acetate, ether, chloroform, and the like. Purification is accomplished by chromatography, e.g. on silica gel.

When a 15-carboxyacylated PGF$\alpha$ acid has been prepared and an alkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, for example, gives the ethyl, butyl and 2-ethylhexyl esters, respectively.

Esterification with diazohydrocarbons is carried out by mixing a solution of the diazohydrocarbon in a suitable inert solvent, preferably ethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley and Sons, Inc., New York, N.Y., Vol. 8, pp. 389–394 (1954).

The final formula-VI compounds prepared by the processes of this invention, in free acid form, are transformed to pharmacologically acceptable salts by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium, salts, amine acid addition salts, and quaternary ammonium salts. The choice of procedure depends in part upon the solubility characteristics of the particular salt to be prepared. In the case of the inorganic salts, it is usually suitable to dissolve the formula-VI acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, the formula-VI acid is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing the formula-VI acid with the stoichiometric amount of the corresponding quaternary ammonium hydroxide in water solution, followed by evaporation of the water.

DESCRIPTION OF THE PREFERRED EMBODIMENTS

The invention can be more fully understood by the following examples.

All temperatures are in degrees centigrade.

Mass spectra are recorded on an Atlas CH-4 mass spectrometer with a TO-4 source (ionization voltage 70 ev.).

EXAMPLE 1

$PGF_{2\alpha}$, 15-Acetate (Formula VI: X is trans—CH=CH—, Y is cis—CH=CH—, Z is —$CH_2CH_2$—,

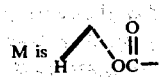

and $R_1$ is hydrogen).

Refer to Chart A.

A. $PGF_{2\alpha}$, 9,11-cyclic butaneboronate.- n-Butaneboronic acid (24 mg.) is added to a solution of $PGF_{2\alpha}$ (48.4 mg.) in 2 ml. of pyridine at about 25° C. The reaction is monitored by gas chromatography (GLC) after conversion of the sample to the trimethylsilyl (TMS) derivative; retention time 7.8 min. on a column of ¼ in. × 17 in. OV-1 (1%) on Gas Chrom Q at 210° C. (compared with 5.3 min. for $PGF_{2\alpha}$, TMS derivative). Concentration of the reaction mixture after one hour yields a residue of $PGF_{2\alpha}$, 9,11-cyclic butaneboronate; mass spectral peaks (TMS derivative): 564, 549, 493, 474, 391, and 372.

B. $PGF_{2\alpha}$, 15-acetate.- Acetic anhydride (2 ml.) is added to a solution of the Example 1A product above in 2 ml. of pyridine and the mixture is left at about 25° C. for 24 hrs. Water (3 ml.) is added and the mixture is concentrated under reduced pressure at 35° C. The oily residue is dissolved in 50 ml. of hexane-ethyl acetate (1:1) and the solution is extracted several times with 50 ml. portions of an aqueous phosphate-citrate buffer at pH 7.5. The combined aqueous phases are acidified to pH 3.5 and extracted several times with ethyl acetate. The combined organic phases are concentrated and the residue is subjected to silica gel chromatography. Elution is with ethyl acetate-acetic acid (97:3). Fractions which are free of starting materials and impurities are combined and concentrated to yield the title compound, an oil; mass spectral peaks (TMS derivative) at 612, 552, 537, 481, and 462.

Following the procedures of Example 1, but replacing n-butaneboronic acid with benzeneboronic acid, there is obtained the formula-IX 9,11-cyclic benzeneboronate, and, subsequently, $PGF_{2\alpha}$, 15-acetate.

Following the procedures of Example 1, but replacing acetic anhydride with benzoic anhydride, there is obtained $PGF_{2\alpha}$, 15-benzoate.

Also following the procedures of Example 1, but replacing acetic anhydride with the various carboxylic acid anhydrides within the scope of

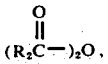

for example propionic, pentanoic, nonanoic, tridecanoic, stearic, (mono, di, and tri) chloroacetic, 3-chlorovaleric, 3-(2-bromoethyl)-4,8-dimethylnonanoic, cyclopropaneacetic, 3-cycloheptanepropionic, 3-cyclopentanetridecanoic, phenylacetic, 2-phenylpropionic, 13-phenyltridecanoic, phenoxyacetic, benzoic, m-bromobenzoic, 2,4-dichlorobenzoic, p-trifluoromethylbenzoic, 2-chloro-3-nitrobenzoic, p-nitrobenzoic, o-toluic, 4-methyl-3-nitrobenzoic, 4-octylbenzoic, 3-biphenylcarboxylic, 3-chloro-4-biphenylcarboxylic, 5-isopropyl-6-nitro-3-biphenylcarboxylic, and 2-naphthoic anhydrides, there are obtained the corresponding formula-X 9,11-cyclic butaneboronates. From them are prepared the corresponding formula-VI 15-carboxyacylates, namely the propionate, pentanoate, nonanoate, tridecanoate, stearate, (mono, di, and tri) chloroacetates, 3-chlorovalerates, 3-(2-bromoethyl)-4,8-dimethylnonanoate, cyclopropaneacetate, 3-cycloheptanepropionate, 13-cyclopentanetridecanoate, phenylacetate, 2-phenylpropionate, 13-phenyltridecanoate, phenoxyacetate, benzoate, m-bromobenzoate, 2,4-dichlorobenzoate, p-trifluoromethylbenzoate, 2-chloro-3-nitrobenzoate, p-nitrobenzoate, o-toluate, 4-methyl-3-nitrobenzoate, 4-octylbenzoate, 3-biphenylcarboxylate, 3-chloro-4-biphenylcarboxylate, 5-isopropyl-6-nitro-3-biphenylcarboxylate, and 2-naphthoate.

Also following the procedures of Example 1, but replacing $PGF_{2\alpha}$ with $15\beta$-$PGF_{2\alpha}$, there is obtained $15\beta$-$PGF_{2\alpha}$, 15-acetate.

Also following the procedures of Example 1, but replacing $PGF_{2\alpha}$ with $PGF_{1\alpha}$, $PGF_{3\alpha}$, and dihydro-$PGF_{1\alpha}$, there are obtained the corresponding 15-acetates namely $PGF_{1\alpha}$, 15-acetate; $PGF_{3\alpha}$, 15-acetate; and dehydro-$PGF_{1\alpha}$, 15-acetate.

Also following the procedures of Example 1 but replacing $PGF_{2\alpha}$ with $PGF_{1\alpha}$, $PGF_{3\alpha}$, and dihydro-$PGF_{1\alpha}$, and also replacing acetic anhydride with each of the carboxy acid anhydrides named following Example 1, there are obtained the corresponding 15-carboxyacylates of those $PGF\alpha$ compounds.

Also following the procedures of Example 1, but replacing $PGF_{2\alpha}$ with the methyl, ethyl, butyl, and octyl esters of $PGF_{2\alpha}$, there are obtained the corresponding methyl, ethyl, butyl, and octyl esters of $PGF_{2\alpha}$, 15-acetate.

EXAMPLE 2

$PGF_{2\alpha}$, 15-Butyrate.

Following the procedures of Example 1 but replacing acetic anhydride with butyric anhydride, there is obtained the title compound, an oil; mass spectral peaks (TMS derivative) at 640, 552, 537, 481, and 462.

EXAMPLE 3

$PGF_{2\alpha}$, 15-Acetate, Methyl Ester.

A solution of $PGF_{2\alpha}$, 15-acetate (Example 1) in ether-methanol (9:1) is treated with diazomethane (about 50% excess) in diethyl ether. After the mixture has stood about 5 min. 25° C. it is concentrated to the title compound; mass spectral peaks (TMS derivative) at 554, 494, 479, 423, 404, and 333.

EXAMPLE 4

$PGF_{2\alpha}$, 15-Hexanoate.

Following the procedures of Example 1 but replacing acetic anhydride with hexanoic anhydride and eluting the chromatographed mixture with ethyl acetate-hexane-acetic acid (75:25:3) there is obtained the title compound, a colorless oil, 102 mg.; mass spectral peaks (TMS derivative) at 552, 537, and 462; TLC $R_f$ 0.3 on silica gel in ethyl acetate-hexane-acetic acid (50:50:3).

EXAMPLE 5

$PGF_{2\alpha}$, 15-Hexanoate, Methyl Ester.

Following the procedure of Example 3, $PGF_{2\alpha}$, 15-hexanoate (Example 4) is transformed with diazomethane to the title compound, a colorless oil, 81 mg.; mass spectral peaks (TMS derivative) at 610, 595, 579, 520, 494, and 479; TLC $R_f$ 0.4 on silica gel in ethyl acetate-hexane-acetic acid (50:50:3).

EXAMPLE 6

$PGF_{2\alpha}$, 15-p-Nitrobenzoate.

p-Nitrobenzoyl chloride (0.3 g.) is added to a solution of $PGF_{2\alpha}$, 9,11-cyclic butaneboronate (0.1 g.) in dry pyridine at about 25° C.

After about 2 hrs., water (3 ml.) is added and the mixture is concentrated under reduced pressure. The residue is dissolved in 50 ml. of hexane-ethyl acetate (1:1) and the solution is extracted several times with 50 ml. portions of an aqueous phosphate-citrate buffer at pH 7.8. The organic phase is dried over sodium sulfate and concentrated under reduced pressure. The residue is subjected to silica gel chromatography, eluting with ethyl acetate-acetic acid (97:3). Fractions which are free of starting materials and impurities are combined and concentrated to yield the title compound; TLC $R_f$ 0.4 on silica gel in ethyl acetate-acetic acid (97:3).

EXAMPLE 7

$PGF_{2\alpha}$, 15-Propionate

Using 505 mg. of $PGF_{2\alpha}$, 350 mg. of phenylboronic acid, 6 ml. of propionic anhydride, and 10 ml. of pyridine, there is obtained 205 mg. of the title compound. Mass spectral peaks at 336, 318, 300, and 264.

EXAMPLE 8

$PGF_{2\alpha}$, 15-Valerate

Using 450 mg. of $PGF_{2\alpha}$, 304 mg. of n-butaneboronic acid, 3 ml. of n-valeric anhydride, and 30 ml. of pyridine, there is obtained 110 g. of the title compound. Mass spectral peaks are at 336, 318, and 264.

EXAMPLE 9

$PGF_{2\alpha}$, 15-Decanoate

Using 300 mg. of $PGF_{2\alpha}$, 201 mg. of n-butaneboronic acid, 2 ml. of n-decanoic anhydride, and 20 ml. of pyridine there is obtained 110 g. of the title compound. Mass spectral peaks are at 336, 318, 300, and 264.

EXAMPLE 10

$PGF_{2\alpha}$, 15-Palmitate

Using 300 mg. of $PGF_{2\alpha}$, 201 mg. of n-butaneboronic acid, 0.5 g. of n-palmitic anhydride, and 20 ml. of pyridine, there is obtained 70 mg. of the title compound. Mass spectral peaks are at 318, 300, and 264.

I claim:

1. An optically active compound of the formula

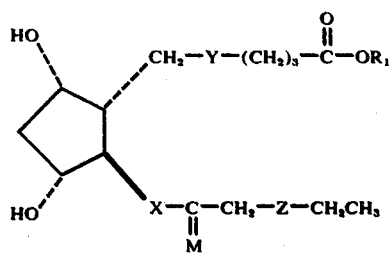

or a racemic compound of that formula and the mirror image thereof, wherein (a) X is trans—CH=CH— or —CH$_2$CH$_2$—, and Y and Z are both —CH$_2$CH$_2$—, or (b) X is trans—CH=CH—, Y is cis—CH=CH—, and Z is —CH$_2$CH$_2$— or cis—CH=CH—; wherein M is

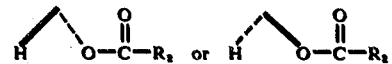

wherein R$_2$ is n-propyl; and wherein R$_1$ is hydrogen or alkyl of one to 8 carbon atoms, inclusive and the pharmacologically acceptable salts thereof when R$_1$ is hydrogen.

2. A compound according to claim 1 wherein X is trans—CH=CH—, Y is cis—CH=CH—, Z is —CH$_2$CH$_2$—, and M is

3. $PGF_{2\alpha}$, 15-butyrate, a compound according to claim 2.

* * * * *